US00PP08420P

United States Patent [19]

Jessel, Jr.

[11] Patent Number: Plant 8,420

[45] Date of Patent: Oct. 12, 1993

[54] CARNATION PLANT NAMED CFPC STANZA

[75] Inventor: Walter H. Jessel, Jr., Salinas, Calif.

[73] Assignee: California Florida Plant Co., L. P., Salinas, Calif.

[21] Appl. No.: 954,349

[22] Filed: Sep. 30, 1992

[51] Int. Cl.[5] ..... A01H 5/00

[52] U.S. Cl. ..... Plt./71.1

[58] Field of Search ..... Plt./70.1, 70.2, 70.5, Plt./71.1, 72.1

*Primary Examiner*—Howard J. Locker

*Attorney, Agent, or Firm*—Christie, Parker & Hale

[57] ABSTRACT

A new carnation of salmon-pink coloration.

1 Drawing Sheet

SUMMARY OF THE INVENTION

The present invention relates to a new and distinct variety of carnation plant which was originated by me in a controlled breeding program by my crossing as seed parent the variety known as 'Londapo' (U.S. Plant Pat. No. 5,515) and as pollen parent the variety known as 'Castellaro' (U.S. Plant Pat. No. 5,762). The varietal denomination of this new carnation is 'CFPC Stanza.'

Among the novel combination of characteristics possessed by the new variety which distinguishes it from its parents and all other varieties of which I am aware are the attractive salmon-pink flower coloring, which fades out smoothly when fully mature. Flowers have a low percentage of splitting and a high percentage (about 95%) of cut flower grade "fancy." Peduncles are relatively short, thus making it easy to remove lateral buds.

Asexual reproduction by propagation by side-shoot cuttings of the new variety as performed in Salinas, Calif. shows that the foregoing and other distinguishing characteristics come true to form and are established and transmitted through succeeding propagations. Although propagation by side-shoot cuttings is described, other known methods of asexual reproduction may also be used to reproduce 'CFPC Stanza.'

BRIEF DESCRIPTION OF THE ILLUSTRATION

The accompanying illustration shows a typical specimen of the flower of the new variety in full bloom depicted in color as nearly true as it is reasonably possible to make the same in a color illustration of this character.

DESCRIPTION OF THE NEW VARIETY

The following is a detailed description of my new variety, with color terminology in accordance with The Royal Horticultural Society Colour Chart (R.H.S.C.C.). The terminology used in the color descriptions herein refers to plate numbers in the aforementioned color chart. Color designations and color descriptions may deviate from the stated values depending upon varying environmental, seasonal and cultural conditions.

The information provided herein is based on observations of plants grown inside commercial greenhouses at Fremont and Salinas, Calif. The height of plant and flower and foliage size are established as an average using standard commercial cultural practices.

Name: 'CFPC Stanza'.

Classification:

*Botanical.*—*Dianthus caryophyllus.*

*Commercial.*—Carnation, standard disbud type.

Parentage:

*Female parent.*—'Londapo'.

*Male parent.*—'Castellaro'.

Plant:

*Height.*—About 35 inches.

*Growing habit.*—Herbaceous, first cut upright.

*Blooming habit.*—Standard disbud type.

*Blooming season.*—Year-round.

*Rooting time.*—About 16–17 days.

*Mutation prone.*—Does not appear to be.

*Disease resistance.*—Better than average.

*Breaking action.*—Good.

Foliage:

*Color.*—Upper side: Near to 135A. Lower side: Near to 135B.

*Size.*—About 5 inches long.

*Quantity.*—Numerous.

*Shape.*—Lanceolate.

*Texture.*—Smooth.

*Ribs.*—Central, keeled.

*Arrangement.*—Bilateral along stem.

*Stem.*—Green.

Bud:

*Shape.*—Oval.

*Color.*—143A.

*Length.*—About 1¼ inches.

*Diameter.*—About ¾ inch.

Calyx:

*Number of sepals.*—About 5.

*Length.*—About 1 inch.

*Width.*—About ½ inch.

*Color.*—Outside — Near to 146D. Inside — Near to 149D.

Bloom:

*Shape.*—Round.

*Size.*—Diameter average: About 3 to 3½ inches. Depth average: About 1¼ inches.

*Borne.*—Terminal as a standard.

*Color.*—General tonality: Salmon pink. Upper side: Near to 56C. Lower side: Near to 56D. Center: Near to 56C. Outer petals: Near to 56C.

*Keeping quality.*—Excellent.

*Fragrance.*—Slight.

Petals:

*Number.*—About 67.

*Outer petals.*—Length: About 1¼ inches. Width: About 1 inch.

*Central petals.*—Length: About 1½ inches. Width: About 1 inch.

*Texture.*—Smooth.

*Form.*—Fan-shaped.

*Appearance.*—Shiny.

Reproductive organs (not visible in this variety):

*Stamens.*—Number: 11. Arrangement: Around the ovary.

*Anthers.*—Length: About ⅛ inch. Color: Near to 161D.

*Filaments.*—Length: About 1 inch. Color: Near to 155D.

*Pistil.*—Number: About 2. Color: Style — Near to from 158C to white. Length: About 1 inch at maturity.

*Stigma.*—Number: About 2. Color: Near 36C.

*Ovary.*—Shape: Conical, ribbed. Color: Base — Greenish white. Body — Greenish yellow. Apex — Tan.

*Fertility.*—Male: Sterile. Female: Sterile.

I claim:

1. A new and distinct variety of carnation plant, substantially as shown and described.

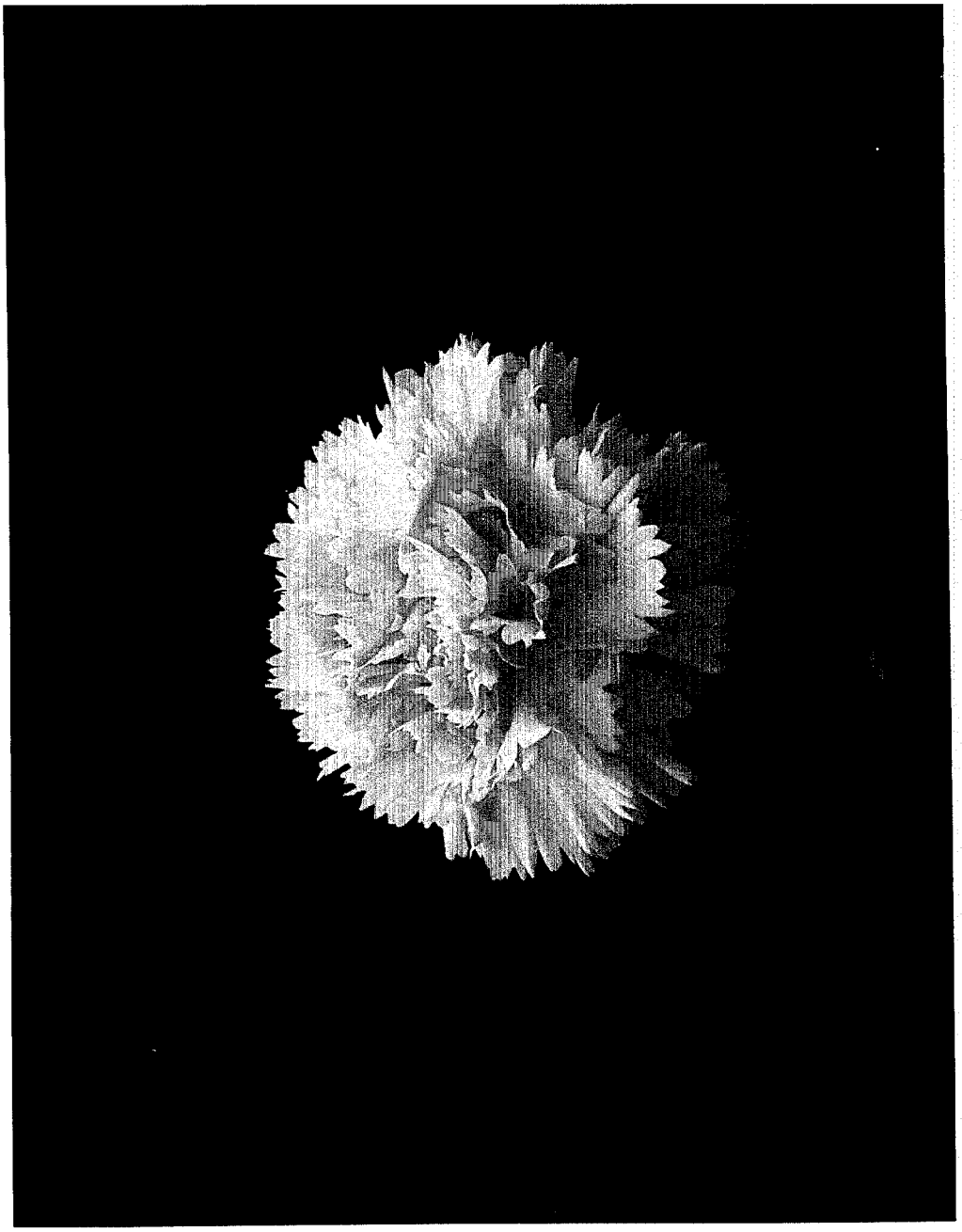

* * * * *